(12) United States Patent
Simon et al.

(10) Patent No.: US 7,371,413 B2
(45) Date of Patent: May 13, 2008

(54) ANTIOXIDANT AND ANTI-INFLAMMATORY ACTIVITY OF COMPOUNDS AND PREPARATIONS FROM AFRICAN NUTMEG SEEDS

(75) Inventors: James E. Simon, Princeton, NJ (US); Mingfu Wang, Piscataway, NJ (US); Kodzo Gbewonyo, Somerset, NJ (US); Mohamed M. Rafi, Highland Park, NJ (US); Daniel Fahene Acquaye, Accra (GH); Yaw Asianowa, Kumasi (GH)

(73) Assignees: Rutgers, The State University, New Brunswick, NJ (US); BioResources International Inc., Somerset, NJ (US)

( * ) Notice: Subject to any disclaimer, the term of this patent is extended or adjusted under 35 U.S.C. 154(b) by 194 days.

(21) Appl. No.: 10/839,056

(22) Filed: May 5, 2004

(65) Prior Publication Data

US 2005/0003030 A1    Jan. 6, 2005

Related U.S. Application Data

(60) Provisional application No. 60/468,049, filed on May 5, 2003, now abandoned.

(51) Int. Cl.
*A61K 36/00*     (2006.01)
(52) U.S. Cl. ..................................................... 424/725
(58) Field of Classification Search ..................... None
See application file for complete search history.

(56) References Cited

U.S. PATENT DOCUMENTS

| | | |
|---|---|---|
| 6,489,494 B1 | 12/2002 | Leonard |
| 6,713,512 B1 | 3/2004 | Leonard |
| 2003/0129294 A1 | 7/2003 | Barclay et al. |
| 2003/0181521 A1 | 9/2003 | Leonard et al. |
| 2003/0206936 A1 | 11/2003 | Barclay et al. |

*Primary Examiner*—Susan Coe Hoffman
(74) *Attorney, Agent, or Firm*—Venable LLP; Michael A. Gollin; Lars H. Genieser (57) ABSTRACT

The present invention provides methods for reducing the production of nitric oxide, inducible nitric oxide synthase protein and mRNA, and cyclooxygenase-2 protein and mRNA in cells both in vivo and in vitro via the administration of extracts and compounds derived from the seeds of *Pycnanthus angolensis* Warb. (*P. Kombo*), commonly known as African nutmeg. These extracts and compounds, namely, *kombo* butter, *kombo* butter acid extract, sargaquinoic acid, sargachromenol, and sargahydroquinoic acid, are also useful in the treatment and prevention of a battery of adverse health conditions in human, animal, and avian subjects that are advanced by the production of nitric oxide or its metabolites and/or by the activity of cyclooxygenase-2. Methods for the isolation of *kombo* butter acid extracts are also provided.

12 Claims, 7 Drawing Sheets

Figure 1. Structure of Sargaquinoic acid (KB-1)

Figure 2. Structure of Sargachromenol (KB-2)

Figure 3. Structure of Sargahydroquinoic acid (KB-3)

Figure 4. Inhibition of NO production in LPS-induced RAW 264.7 cells by Sargaquinoic Acid (KB-1). ([LPS] = 0.5 μg/mL)

Figure 5. Inhibition of NO production in LPS-induced RAW 264.7 cells by Sargachromenol (KB-2). ([LPS] = 0.5 μg/mL)

Figure 6. Inhibition of NO production in LPS-induced RAW 264.7 cells by Sargahydroquinoic Acid (KB-3). ([LPS] = 0.5 μg/mL)

Figure 7. Inhibition of NO production in LPS-induced RAW 264.7 cells by Kombo Butter. ([LPS] = 0.5 µg/mL)

Figure 8. Inhibition of NO production in LPS-induced RAW 264.7 cells by Kombo Butter Acid Extract. ([LPS] = 0.5 µg/mL)

| LANE # | IDENTITY | % Protein Expression ||
|---|---|---|---|
| | | iNOS | COX-2 |
| 1 | LPS (-) Control | 21.6 | 6.1 |
| 2 | LPS (0.5 µg/mL) | 100.0 | 100.0 |
| 3 | LPS + 25 uM Sargaquinoic Acid (KB-1) | 127.4 | 122.2 |
| 4 | LPS + 50 uM Sargaquinoic Acid (KB-1) | 62.0 | 97.5 |
| 5 | LPS + 25 uM Sargachromenol (KB-2) | 95.1 | 115.0 |
| 6 | LPS + 50 uM Sargachromenol (KB-2) | 159.6 | 88.8 |
| 7 | LPS + 25 uM Sargahydroquinoic Acid (KB-3) | 93.5 | 42.4 |
| 8 | LPS + 50 uM Sargahydroquinoic Acid (KB-3) | 47.5 | 18.4 |

Figure 9. Inhibition of iNOS and COX-2 protein expression in LPS-induced RAW 264.7 cells by Sargaquinoic Acid (KB-1), Sargachromenol (KB-2), and Sargahydroquinoic Acid (KB-3). ([LPS] = 0.5 µg/mL)

| LANE # | IDENTITY | % Protein Expression ||
|---|---|---|---|
| | | iNOS | COX-2 |
| 1 | LPS (0.5 µg/mL) | 100.0 | 100.0 |
| 2 | LPS + 5 ug/mL Kombo Butter | 101.3 | 70.1 |
| 3 | LPS + 10 ug/mL Kombo Butter | 59.6 | 59.2 |
| 4 | LPS + 5 ug/mL Kombo Butter Acid Extract | 225.7 | 69.3 |
| 5 | LPS + 10 ug/mL Kombo Butter Acid Extract | 59.5 | 55.7 |
| 6 | LPS + 25 uM Vitamin E | 137.6 | 59.5 |
| 7 | LPS + 50 uM Vitamin E | 119.4 | 68.6 |
| 8 | LPS + 12.5 uM Indomethacin | 64.7 | 54.1 |
| 9 | LPS + 25 uM Indomethacin | 70.2 | 47.7 |

Figure 10. Inhibition of iNOS and COX-2 protein expression in LPS-induced RAW 264.7 cells by Kombo Butter and Kombo Butter Acid Extract. ([LPS] = 0.5 µg/mL)

| LANE # | IDENTITY | % iNOS mRNA Expression |
|---|---|---|
| 1 | LPS (-) Control | 0.0 |
| 2 | LPS ( 0.5 µg/mL) | 100.0 |
| 3 | LPS + 25 uM Sargaquinoic Acid (KB-1) | 125.9 |
| 4 | LPS + 50 uM Sargaquinoic Acid (KB-1) | 83.0 |
| 5 | LPS + 25 uM Sargachromenol (KB-2) | 101.2 |
| 6 | LPS + 50 uM Sargachromenol (KB-2) | 65.4 |
| 7 | LPS + 25 uM Sargahydroquinoic Acid (KB-3) | 68.6 |
| 8 | LPS + 50 uM Sargahydroquinoic Acid (KB-3) | 25.9 |
| 9 | LPS + 5 ug/mL Kombo Butter | 57.1 |
| 10 | LPS + 10 ug/mL Kombo Butter | 19.3 |
| 11 | LPS + 5 ug/mL Kombo Butter Acid Extract | 48.7 |
| 12 | LPS + 10 ug/mL Kombo Butter Acid Extract | 51.0 |
| 13 | LPS + 25 uM Vitamin E | 45.5 |
| 14 | LPS + 50 uM Vitamin E | 45.0 |
| 15 | LPS + 12.5 uM Indomethacin | 44.7 |
| 16 | LPS + 25 uM Indomethacin | 40.3 |

Figure 11. Inhibition of iNOS mRNA expression in LPS-induced RAW 264.7 cells by Kombo Butter and its constituents. ([LPS] = 0.5 µg/mL)

Figure 12. Inhibition of COX-2 mRNA expression in LPS-induced RAW 264.7 cells by Kombo Butter and its constituents. ([LPS] = 0.5 µg/mL)

ANTIOXIDANT AND ANTI-INFLAMMATORY ACTIVITY OF COMPOUNDS AND PREPARATIONS FROM AFRICAN NUTMEG SEEDS

CROSS REFERENCE TO RELATED APPLICATIONS

The present application claims priority under 35 USC §119(e) to U.S. Provisional Application Ser. No. 60/468,049, filed on May 5, 2003, now abandoned which is incorporated by reference in its entirety herein.

FIELD OF THE INVENTION

The present invention is directed to the use of extracts and compounds derived from the seeds of *Pycnanthus angolensis* Warb. (*P. Kombo*), commonly known as African nutmeg, for the prophylaxis and treatment of a battery of adverse health conditions associated with inflammation and/or the presence of free radicals. More particularly, the invention relates to the use of kombo butter, kombo butter acid extract, sargachromenol, sargaquinoic acid, and sargahydroquinoic acid as antioxidants, nitric oxide (NO) scavengers, and inhibitors of the generation of NO, inducible nitric oxide synthase (iNOS), and cyclooxygenase-2 (COX-2), and thus are useful for the prevention and treatment of a variety of adverse health conditions in human, animal, and avian subjects.

BACKGROUND

A considerable amount of epidemiological evidence indicates a strong association between the consumption of a diet rich in fruits and vegetables and decreased risks of cardiovascular disease and cancer. It is generally believed that the primary agents giving rise to these beneficial health effects are phytochemical antioxidants. These compounds effectively neutralize free radicals, active atoms or molecules that can damage DNA and corrode cell membranes. Free radicals play a key role in the development of a number of adverse health conditions, including cancer, cardiovascular disease, and cataracts, and have also been implicated in both initiation and acceleration of the aging process. The results of an extensive body of research indicate the existence of a variety of beneficial properties of free radical scavengers and antioxidants, including anti-mutagenic, anti-inflammatory, anti-atherosclerotic, anti-diabetic, anti-hepatotoxic, and anti-aging properties, as well as the utility of such agents in a variety of neurological disorders. Given the wide range and gravity of the adverse health conditions associated with free radicals and other inflammatory factors, there is a critical need for agents capable of exerting antioxidant and anti-inflammatory effects to improve the pharmacological treatment of conditions such as cancer, cardiovascular disease (including atherosclerosis), cataracts, rheumatic diseases, fibromyalgia, inflammatory bowel syndrome, and Alzheimer's disease as well as numerous other neurodegenerative conditions.

Important mediators in the inflammatory response include nitric oxide (NO) and prostaglandins (PGs), which are produced at elevated levels during inflammation. Nearly two decades ago, NO was found to be released by the vascular endothelium and to be a mediator of vasodilator-induced relaxation. Thus, NO is now widely known as endothelium-derived relaxing factor and the endogenous production of NO has been shown to play an essential role in physiological regulation and host defense mechanisms. In innate immunity, production of NO counters microbial and parasitic invasion and is associated with cytotoxic and cytostatic activities against bacteria and tumor cells. Additionally, increasing evidence indicates the importance of NO in the modulation of inflammation and the overproduction of NO has been found during the progress of many inflammatory diseases such as rheumatoid arthritis and osteoarthritis.

NO is a short-lived free radical produced from L-arginine in a reaction catalyzed by NO synthase (NOS). NO mediates diverse functions by acting on most cells of the body via interaction with a variety of molecular targets that are consequently either activated or inhibited [1]. At least three types of NOS isoforms have been reported [2]. Endothelial NOS and neuronal NOS are constitutively expressed and are $Ca^{2+}$/calmodulin dependent, whereas expression of the high-output isoform, inducible NOS (iNOS) occurs in activated macrophages and endothelial cells following induction by cytokines such as interferon (IFN) α, β, and γ, interleukin (IL)-1α and -1β, and lipopolysaccharide (LPS) [3]. Low concentrations of NO produced by iNOS are implicated in the antimicrobial activity of macrophages against pathogens [4]. Excessive production of NO and its derivatives, such as peroxynitrite and nitrogen dioxide, has been suggested to be mutagenic in vivo, and to provoke the pathogenesis of septic shock and diverse autoimmune disorders [5-8]. Furthermore, NO and its oxidized forms have also been shown to be carcinogenic [9]. Therefore, key therapeutic targets for such adverse conditions include the reduction of NO activity by neutralization of NO as well as reduction of the generation of NO via inhibition of iNOS activity and/or inhibition of iNOS expression.

PGs are important inflammatory mediators that are synthesized from fatty acid precursors via the cyclooxygenase pathway. Two different isoforms of cyclooxygenase (COX), designated cyclooxygenase-1 (COX-1) and cyclooxygenase-2 (COX-2), have been identified. COX-1 is a constitutive isoform that exists in most tissues and is responsible for the production of prostanoids involved in homeostasis. COX-2 is undetectable in most normal tissues, but is induced by cytokines, growth factors, oncogenes and tumor promoters, and is responsible for the production of prostanoids involved in inflammation. Enhanced levels of COX-2 have been found in humans during the course of numerous inflammatory conditions including rheumatoid arthritis, osteoarthritis and acute or chronic inflammatory disease. As the induction of COX-2 is responsible for the production of PGs at the site of inflammation, this enzyme, like iNOS, represents a possible target for therapeutic purposes [10].

Although the use of herbal therapy or alternative medicine represents an increasingly attractive approach for the treatment of various inflammatory disorders, there is often little scientific data to support such uses. Accordingly, we have investigated plants and botanical extracts to identify specific compounds possessing bioactivities applicable to the treatment of inflammatory disorders and to understand the biochemical mechanisms of such activities. Anti-inflammatory properties of various phytochemicals are mediated through inhibition of the production of cytokines (IL-1β, TNF-α, IL-6, IL-12, IFN-γ), nitric oxide (NO), prostaglandins and leukotrienes [11]. Antioxidants such as (−)-epigallocatechin-3-gallate (EGCG) [12], resveratrol [13] and naturally occurring flavonoids including apigenin and kaempferol [14] have been reported to suppress NO production through inhibition of NF-κB.

*Pycnanthus angolensis* Warb. (*P. Kombo*), commonly known as African nutmeg, is a tropical plant belonging to the Myristicaceae family and having a geographical distribution stretching across western Africa from Guinea to Cameroon, including the countries of Sierra Leone, Liberia, Cote D'Ivoire, Ghana, Togo, Benin, Nigeria, Equatorial Guinea, Angola and Uganda [15]. The plant thrives well in secondary forests, growing up to 120 feet tall, and produces fruit annually, typically between September and April. The oblong-shaped fruits, about 1.5 inches long, contain oil-rich seeds encased in a hard shell. The seeds are ready for harvest between December and April. The indigenous populations have devised a variety of uses for virtually all parts of the plant, ranging from incorporation of the plant in furniture, condiments, soaps, and cattle feed to medicinal uses.

Traditional medicinal uses for the plant utilize the bark, roots, leaves, and seeds. The pounded bark is used by the Ibos of Nigeria as a mouthwash and also as a remedy for toothaches and appetite loss. Infusions of the bark are used to prevent abortions, anemia, headache, and scabies [16]. Decoctions of the bark are used as an enema to purify breast milk for nursing mothers, as a purgative, and as an antidote for poisons. Other uses include the treatment of body aches, chest pains, skin lesions, and rashes due to river blindness (Onchocercearsis) and leprosy. Root infusions containing additional herbs are used as an antihelmintic [17]. Decoctions of the leaves are used as an enema to treat toothache and prevent miscarriage. The leaf juice is sucked to cure white tongue thrush and the latex is applied to wounds as an anticoagulant [17]. The Ewes in Ghana use fat from the oil-rich seeds as a mouthwash to cure thrush and as a topical treatment for fungal skin infections. In addition to such medicinal uses, the seeds provide an important source of oil and wax in the local communities for making candles, soap, fuel and lubricants. The oil residue is used as manure and cattle feed, and there are also reports of its use as a condiment in Equatorial Guinea.

Relatively few studies have investigated the chemical components of *Pycnanthus angolensis*. Two terpenoid-type quinines (pycnanthoquinone A and B) with antihyperglycemic activity have been isolated from the leaves and stem extracts [18,19] and the lignan dihydroguaiaretic acid has been identified in a bark extract [20]. Two isoflavones, 2'-hydroxyformononetin and 7,4'-dimethoxy-2'-hydroxyisoflavone, have been identified in the heartwood of the plant [21]. The seed fat is characterized by the presence of relatively high contents of tetradecanoic acid (60%) and (Z)-9-tetradecenoic acid (20%) as well as other unsaturated fatty acids [22,23,24]. A recent study of the seed fat identified a novel polyphenylated hydroquinone carboxylic acid named kombic acid [24], although the structure of this compound as reported there is questionable based on our own research findings. We have discovered that *kombo* butter, *kombo* butter acid extract, and three compounds, sargaquinoic acid, sargachromenol, and sargahydroquinoic acid, from the seeds of African nutmeg possess activity as antioxidants, NO scavengers, and inhibitors of the production of NO, iNOS, and COX-2, and are thus useful for the prevention and treatment of a number of adverse health conditions linked to inflammation in human, animal, and avian subjects.

The anti-inflammatory and antioxidant activities of sargachromenol and sargahydroquinoic acid isolated from *Roldana barba-johannis* have been evaluated [25]. The anti-inflammatory activity of sargachromenol exceeded that of α-tocopherol, and that of sargahydroquinoic acid was on par with that of a-tocopherol as measured by the TPA-induced mouse ear edema assay. Both of these compounds had less anti-inflammatory activity than indomethacin. The antioxidant activities of these compounds, as measured by the DPPH radical scavenging assay, were found to be better than those of either α-tocopherol or indomethacin. The authors noted that the anti-inflammatory activities of sargachromenol and sargahydroquinoic acid could be related both to their ability to scavenge free radicals and to their possible interaction with enzymes that catalyze the formation of intermediaries in the inflammatory process.

U.S. Pat. No. 6,489,494 to Leonard discloses antioxidants comprising kombic acid, a substituted palmitic fatty acid, or derivatives thereof obtained from crude *kombo* butter, as well as methods for the isolation of such antioxidants from crude *kombo* butter. Leonard found that the solubility of kombic acid in either alcohol or supercritical carbon dioxide was much less than that of more common fatty acids and glycerides, and thus that extraction with either of these solvents represented a commercially viable means for the isolation of kombic acid from *kombo* butter. Leonard also showed that the antioxidant activity of kombic acid with respect to lipid peroxidation either met or exceeded that of α-tocopherol in in vitro assays, and that kombic acid was an effective antioxidant for the stabilization of edible oils, plastics, and cosmetics. U.S. Pat. No. 6,713,512 to Leonard, a continuation-in-part of the '494 patent, discloses the use of kombic acid and derivatives thereof as anticancer and cholesterol-lowering agents.

Published United States Patent Application No. 20030129294A1 to Barclay et al. discloses blends comprising triglycerides and a hydroquinone substituted polyunsaturated fatty acid, as present in *kombo* butter, or a derivative thereof. A particularly preferred substituted fatty acid is sargahydroquinoic acid. Additionally, the blends may comprise glycerides from *kombo* butter and/or antioxidant compounds to stabilize the acids of the invention. Also disclosed are food products and dietary supplements having a health component that is a hydroquinone substituted polyunsaturated fatty acid as present in *kombo* butter, extracts thereof, or a derivative thereof, and particularly sargahydroquinoic acid. Barclay discloses the activity of sargahydroquinoic acid as an inhibitor of pancreatic lipase, a stimulant for increased production of the dermal protein decorin, a ligand for peroxisome proliferator activated receptor (PPAR) subtypes α and γ, an inhibitor of cholesterol esterase and acetylcholine esterase, and an inhibitor of microbial viability and fatty acid catabolism. In light of these findings, Barclay postulates the utility of the hydroquinone substituted polyunsaturated fatty acid preparations of the invention in: treatment and prevention of obesity (pancreatic/gastric lipase inhibitor); improved lipid metabolism, control of hyperlipidemia, and treatment and prevention of cancer (PPAR-α ligand); control of insulin sensitivity to avert short-term problems of insulin resistance including cognitive impairment (poor memory), chronic fatigue, and mood swings, as well as long-term problems including cardiovascular disease, type-2 diabetes, and polycystic ovary syndrome (PPAR-γ ligand); improved cognition, improved regulation of blood sugar levels, cellular differentiation, lipid metabolism, and glucose metabolism, and treatment and prevention of inflammation, cancer, gestational diabetes, syndrome X, hypertension, and stroke (also as a PPAR-γ ligand); prevention of aging of the skin due to stimulation of the production of the dermal proteins decorin and collagen; and decreased oral and body odor due to the inhibition of microbial viability and fatty acid catabolism.

Additionally, Barclay discloses the antioxidant activity of a *kombo* nut extract containing approximately 56% sargahydroquinoic acid. Incorporation of 0.5% of the extract in sunflower oil was found to extend the swift induction period for oxidative degradation of the oil from 3 to 17 hours, while incorporation of the same level of a 50% preparation of mixed tocopherols provided only a 4-hour induction period. Barclay also discloses that *kombo* butter saponifiables exhibited a dose-dependent reduction in levels of prostaglandin E2 in human skin fibroblasts after induction with phorbol myristate acetate in vitro. In light of these findings, Barclay postulates the utility of the hydroquinone substituted polyunsaturated fatty acid preparations of the invention in the treatment and prevention of disease conditions relating to inflammation and the presence of free radicals, including cardiovascular disease, joint diseases, arthritis, peptic ulcer disease, inflammatory bowel disease, inflammatory skin conditions, neurodegenerative diseases (including Alzheimer's), and allergies.

Finally, Barclay discloses a process to enrich a hydroquinone substituted polyunsaturated fatty acid from *kombo* butter. According to the process, *kombo* butter is refined by the addition of base at a temperature of 40 to 60° C., and the product is separated into organic and aqueous phases. The aqueous phase is acidified to a pH of 0 to 4, and the oily layer is drained off. This affords recovery of a product containing more than 20% by weight of the hydroquinone substituted polyunsaturated fatty acid.

Published United States Patent Application No. 20030206936A1 to Barclay et al. discloses cosmetic compositions comprising an effective amount of a hydroxy phenyl alkyl carboxylic acid, preferably sargahydroquinoic acid or a derivative thereof. The cosmetic benefits disclosed for such active compounds include: treating and preventing wrinkling, sagging, aging and/or photodamaging of skin; boosting the production of collagen and decorin in the skin; soothing irritated, red and/or sensitive skin; improving skin or scalp texture, smoothness, and firmness; reducing body odor; reducing or preventing dandruff, spots, and pimples; and lightening skin or preventing the darkening of skin. The use of *kombo* butter, its partial glycerides, or its free fatty acids to obtain these cosmetic health benefits is also disclosed. Mirroring the disclosure of the previous Barclay application (No. US20030129294A1) discussed above, examples are presented indicating the utility of sargahydroquinoic acid as a stimulant for increased production of the dermal protein decorin and as a ligand for PPAR subtypes α and γ, as well as the dose-dependent reduction of prostaglandin E2 (PGE2) levels by *kombo* butter saponifiables in human skin fibroblasts in vitro.

Published United States Patent Application No. 20030181521A1 to Leonard et al. discloses the use of cetyl myristoleate from *kombo* butter for the treatment of osteoarthritis and orthopedic or muscular injuries in equines. Leonard found that *kombo* butter-based cetyl myristoleate preparations were much more palatable to horses than preparations derived from beef tallow, thus making ingestion a feasible route of administration for the compound.

Despite the aforementioned references, nothing in the prior art discloses the ability of *kombo* butter, *kombo* butter acid extract, sargaquinoic acid, sargachromenol, or sargahydroquinoic acid to inhibit the production of NO and the expression of iNOS protein and/or mRNA. Moreover, although the Barclay applications disclose the ability of *kombo* butter saponifiables to reduce the levels of PGE2 in human skin fibroblasts in vitro, the use of *kombo* butter, *kombo* butter acid extract, sargachromenol, and sargahydroquinoic acid to reduce COX-2 protein and/or mRNA expression is unknown in the prior art. Thus, we have discovered that *kombo* butter, *kombo* butter acid extract, sargaquinoic acid, sargachromenol, and sargahydroquinoic acid are useful in reducing NO levels during inflammation not only by radical scavenging, but also advantageously by acting to reduce the levels of NO production in response to inflammatory stimuli at the levels of transcription and translation of iNOS. We have also discovered that *kombo* butter, sargachromenol, and sargahydroquinoic acid effectively inhibit both COX-2 protein and mRNA expression and that *kombo* butter acid extract also inhibits expression of the COX-2 enzyme.

SUMMARY OF THE INVENTION

The present invention is directed to beneficial health products and applications arising from our discovery that *kombo* butter, derived from the seeds of *Pycnanthus angolensis* Warb. (*P. Kombo*), commonly known as African nutmeg, as well as *kombo* butter acid extract and each of three pure compounds from *kombo*, namely, sargaquinoic acid, sargachromenol, and sargahydroquinoic acid, possess significant antioxidant and anti-inflammatory activities. We have determined that these preparations and compounds possess significant antioxidant activity as evidenced by their radical scavenging activities in both the 2,2'-diphenylpicrylydrazyl (DPPH) and 2,2'-azinobis-(3-ethylbenzothiazoline-6-sulfonic acid) (ABTS) free radical scavenging assays. Moreover, we have determined that these agents possess significant anti-inflammatory activities as evidenced by a battery of in vitro experiments utilizing lipopolysachharide-induced RAW 264.7 mouse macrophage cells. Specifically, we investigated the effects of the claimed preparations and compounds on levels of nitric oxide (NO) production as well as inducible nitric oxide synthase (iNOS) and cyclooxygenase-2 (COX-2) protein and mRNA expression in these cells. With minor exceptions, notably the effects of *kombo* butter acid extract on COX-2 mRNA expression, the effects of sargaquinoic acid on COX-2 mRNA and protein expression, and the effects of sargachromenol on iNOS protein expression, we have found that each of these agents is active in reducing NO production, iNOS protein and mRNA expression, and COX-2 protein and mRNA expression.

We have thus determined that these preparations and compounds are useful in reducing the production of NO, iNOS protein and mRNA, and COX-2 protein and mRNA in cells that occurs as part of the inflammatory response. Accordingly, these agents possess beneficial inhibitory activities on the inflammatory response in cells, both in vitro and in vivo. Moreover, these agents are useful in the prophylaxis and treatment of a battery of adverse health conditions in human, animal, and avian subjects associated with inflammation and/or the presence of free radicals. Specifically, these agents have application in the treatment and prevention of cancers, particularly colon cancer, arthritis, including osteoarthritis, cardiovascular disease, high blood pressure, atherosclerosis, thromboembolic disease, fibromyalgia, irritable bowel syndrome or inflammatory bowel disease, cataracts, and conditions embodied by decreased cognitive functioning, including Alzheimer's disease as well as numerous other neurodegenerative conditions. Additionally, these agents are applicable to the treatment and prevention of numerous other adverse health conditions, including inflammatory and non-inflammatory rheumatoid and rheumatoid-like conditions as well as conditions embodied by chronic, acute, and/or transitory inflammation.

The preparations and compounds of the present invention can be administered either topically or systemically, and thus have utility as dietary supplements and beneficial health ingredients in foods, cosmetics, and personal health care products, including but not limited to body lotions, oils, shampoos, soaps, lip balms, lipsticks, and skin and muscle creams and ointments. Such formulations may contain any of the active agents of the invention either individually or in admixture with each other and/or with other anti-inflammatory and antioxidant agents including but not limited to *Boswallia serrata* extracts, *Pygeum africanum*, white willow extract, refined or unrefined shea butter or shea butter extract, glucosamine, chondroitin sulfate, Rooibos tea, Rooibos extract (fermented and green), honeybush, green tea, black tea, grape seed extracts, and extracts of blueberries, cranberries, and strawberries. Moreover, sargaquinoic acid, sargachromenol, or sargahydroquinoic acid may be present in the formulation as an extract, a chemical fraction or subfraction of an extract, a purified compound, or a precursor form of the compound capable of chemical transformation into the compound. Finally, we also describe purification protocols to isolate the active preparations and compounds of the invention in high yield either from *kombo* butter or directly from African nutmeg seeds.

DETAILED DESCRIPTION OF THE INVENTION

Preparation of *Kombo* Butter from African Nutmeg Seeds

*Kombo* butter was prepared from African nutmeg seeds (also referred to as *kombo* seeds) by several methods including, but not limited to, aqueous extraction, non-polar solvent extraction, and mechanical pressing. The yield of *kombo* butter obtained via these extraction procedures was generally in the range of 33-60% by weight of the starting material. An appreciable amount of yield loss (10-15%) resulted from oil retention in the filtration step. African nutmeg seeds were harvested and washed thoroughly with water. The clean seeds were dried and ground into a fine paste using a mechanical mill. Three extraction methods were then alternately applied to the *kombo* seeds to recover the *kombo* seed oil, otherwise known as *kombo* butter.

During aqueous extraction, excess water (approximately twice the paste volume) was added to the ground paste and brought to a boil in large open pans for several hours as oil rose to the surface of the liquid. The emerging oil phase was intermittently skimmed off the top of the boiling liquid into a separate receiving container until the oil was depleted from the boiling extract. The oil collected was passed through cheesecloth filters while hot to remove any debris from the oil extract. The filtered oil was then allowed to cool and solidify into a reddish-brown butter.

During solvent extraction, petroleum ether was added to the ground paste and extraction was allowed to proceed for several minutes. The ether extract was decanted from the solid residue and then filtered. Upon evaporation of the solvent, the reddish-brown butter was obtained.

To process multi-kilogram quantities of *kombo* butter, the ground paste was subjected to mechanical pressure in an oilseed press to separate the oil from the solid residue. The mechanical press employed was identical to screw presses commonly used for processing oil palm and shea butter. The oil was then filtered into a collecting vessel. Since *kombo* butter is highly viscoelastic and tends to solidify quickly, it was necessary to supply heat via steam heat exchangers to maintain the oil in a free-flowing state during filtration of the butter.

Preparation of *Kombo* Butter Acid Extracts

*Kombo* butter acid extracts can be prepared from the *kombo* butter obtained as previously described. First, the *kombo* butter is extracted using 70-100% ethanol:water, preferably 95% ethanol:water. When we subjected *kombo* butter to extraction with 95% ethanol:water, we obtained a reddish-brown solution separately from an insoluble fraction that solidified to a pale-yellow fat. When we evaporated the reddish-brown solution, we obtained a crude *kombo* butter extract, a reddish-brown liquid that amounted to approximately 37% by weight of the *kombo* butter. The reddish-brown solution containing the crude extract in 70-100% ethanol:water is then extracted with a non-polar organic solvent such as petroleum ether, hexane, or chloroform, preferably petroleum ether. Upon evaporation of the ethanolic layer, the residue is washed with dilute aqueous base, preferably 5-30% NaOH solution, at which point the *kombo* butter acids are mainly present as their respective salts in aqueous solution. The *kombo* butter acids are recovered by acidifying the solution with an inorganic acid and extracting the acidified solution with a non-polar organic solvent such as petroleum ether, hexane, or chloroform. Upon evaporation of the organic solvent fraction, a *kombo* butter acid extract is obtained which typically contains 0.5-2% sargaquinoic acid, 5-10% sargachromenol, and 30-50% sargahydroquinoic acid with a reddish-brown liquid.

We have also obtained *kombo* butter acid extracts directly from the ground paste of *kombo* seeds without first preparing *kombo* butter via direct extraction of the ground paste with 70-100% ethanol:water. Direct extraction of the ground paste with 95% ethanol followed by the addition of petroleum ether provides two separate phases. The ethanol layer is decanted and evaporated to yield a viscous reddish-brown liquid constituting 20% by weight of the ground paste. Evaporation of the petroleum ether layer yields a pale-yellow solid fat constituting 36% by weight of the ground paste. We have discovered that the viscous reddish-brown liquid obtained from the ethanol layer dissolves readily in dilute aqueous base, preferably 5-30% NaOH, more preferably 10% NaOH, whereas the pale-yellow solid fat is much less soluble, giving a cloudy solution that lathers with vigorous shaking. The solubility difference between these two fractions presents a second means for the isolation of a *kombo* butter acid extract directly from the *kombo* seeds without prior preparation of *kombo* butter. Accordingly, we have also developed a simple method for the separation of *kombo* butter acids from the ground paste of *kombo* seeds as an aqueous extract prior to oil extraction. The *kombo* butter acids can then be reclaimed from the solution of aqueous base by acidification and subsequent extraction with a non-polar solvent as previously described herein.

Isolation of Individual Components from *Kombo* Butter Acid Extracts

Using thin layer chromatography (TLC), silica gel column chromatography, reverse phase silica gel chromatography, Sephadex LH-20 gel filtration chromatography and reverse phase preparative HPLC, we isolated three pure compounds from the *kombo* butter acid extracts prepared as previously described. We determined the structures of these compounds using MS, $^1$H-NMR, $^{13}$C-NMR, and 2D-NMR ($^1$H-$^1$H COSY, HMBC and HMQC) and confirmed their identities as sargaquinoic acid, sargachromenol, and sargahydroquinoic acid by comparison with known spectra. Interestingly, according to our 2D-NMR data, we have determined that the major constituent of *kombo* butter is sargahydroquinoic acid, not kombic acid as reported earlier [24].

Figure 1:
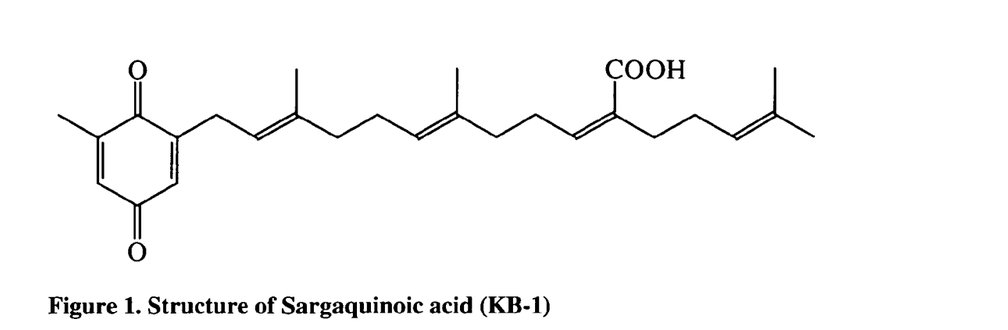
FIG. 1 shows the chemical structure of Sargaquinoic acid (KB-1).

*Kombo* butter acid extract (1 g) was loaded directly onto a silica gel column (60 g of silica gel, 130-270 mesh) and eluted by successive 200 ml portions of hexane-ethyl acetate-acetic acid (8:1:0.1, 6:1:0.1, 4:1:0.1 and 2:1:0.1). A total of 3 subfractions were collected based on the TLC results. Subfraction 1 was further subjected to Sephadex LH-20 gel filtration chromatography using methanol as eluant to obtain two subfractions, 1A and 1B. Subfraction 1B was purified by preparative HPLC on a Phemomenex phenyl-hexyl 30×250 mm, 10 um column using acetonitrile as eluant at a flow rate 10 ml/minute to obtain 10 mg of pure sargaquinoic acid, also referred to herein as compound KB-1. Typical yields of purified sargaquinoic acid were 0.01-1% by weight of the *kombo* butter acid extract. The chemical structure of sargaquinoic acid is presented in FIG. 1.

Figure 2:
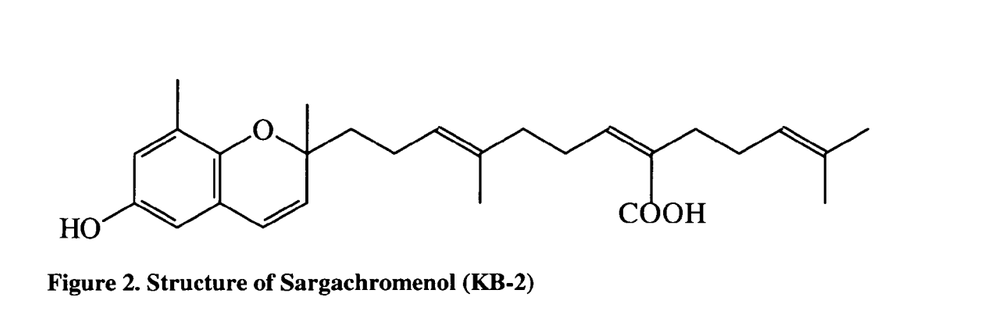
FIG. 2 shows the chemical structure of Sargachromenol (KB-2).

Subfraction 2 was further subjected to Sephadex LH-20 gel filtration chromatography using methanol as eluant. Subsequently, the major component was purified by preparative HPLC on a Phenomenex Phenyl-hexyl 30×250 mm, 10 um column with 80% acetonitrile:water as eluant at a flow rate of 10 ml/min to obtain 40 mg of pure sargachromenol, also referred to herein as compound KB-2. Typical yields of purified sargachromenol were 2-6% by weight of the *kombo* butter acid extract. The chemical structure of sargachromenol is presented in FIG. 2.

Figure 3:
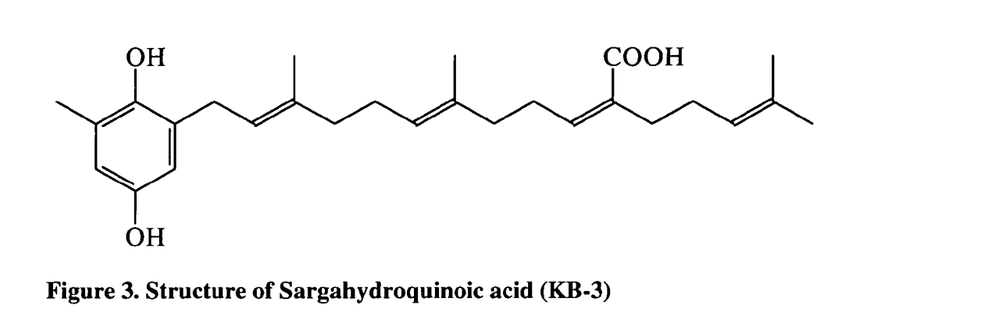
FIG. 3 shows the chemical structure of Sargahydroquinoic acid (KB-3).
Figure 4:
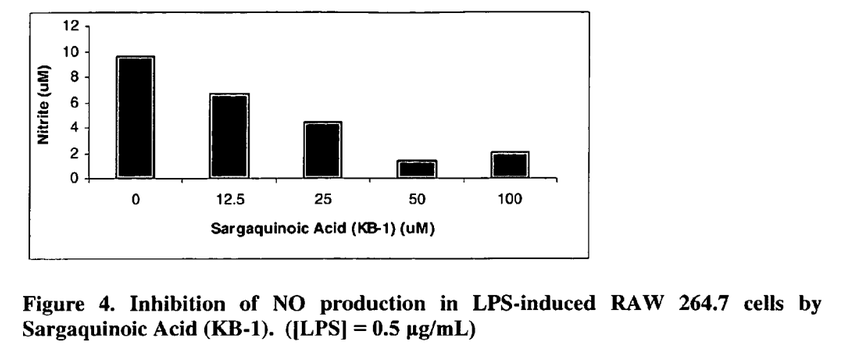
FIG. 4 shows the inhibitory effect of Sargaquinoic acid (KB-1) on nitric oxide production in lipopolysaccharide-induced RAW 264.7 murine macrophage cells.
Figure 5:
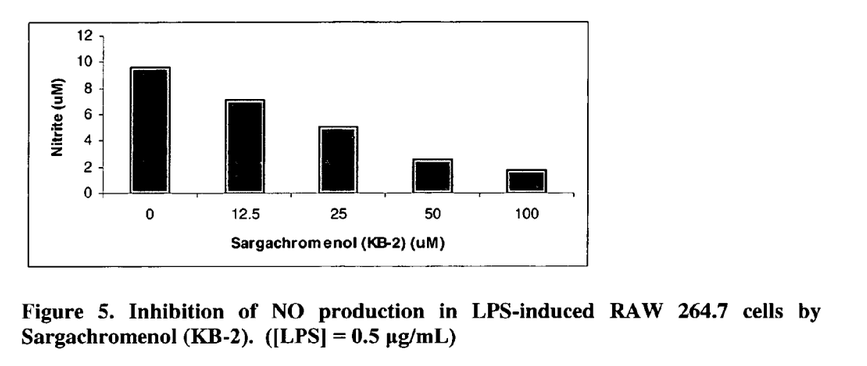
FIG. 5 shows the inhibitory effect of Sargachromenol (KB-2) on nitric oxide production in lipopolysaccharide-induced RAW 264.7 murine macrophage cells.
Figure 6:
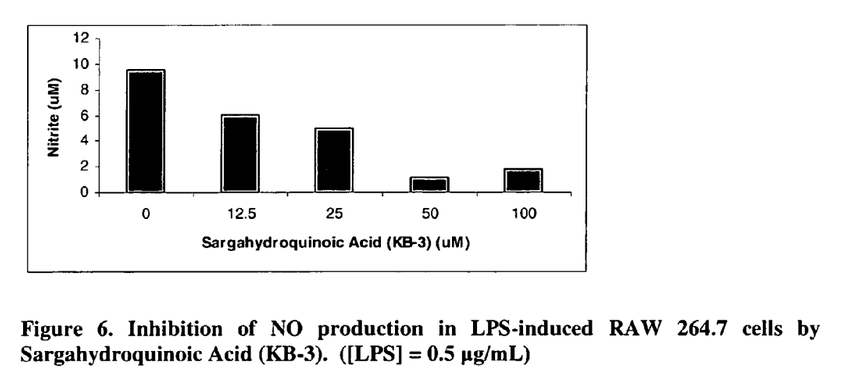
FIG. 6 shows the inhibitory effect of Sargahydroquinoic acid (KB-3) on nitric oxide production in lipopolysaccharide-induced RAW 264.7 murine macrophage cells.
Figure 7:
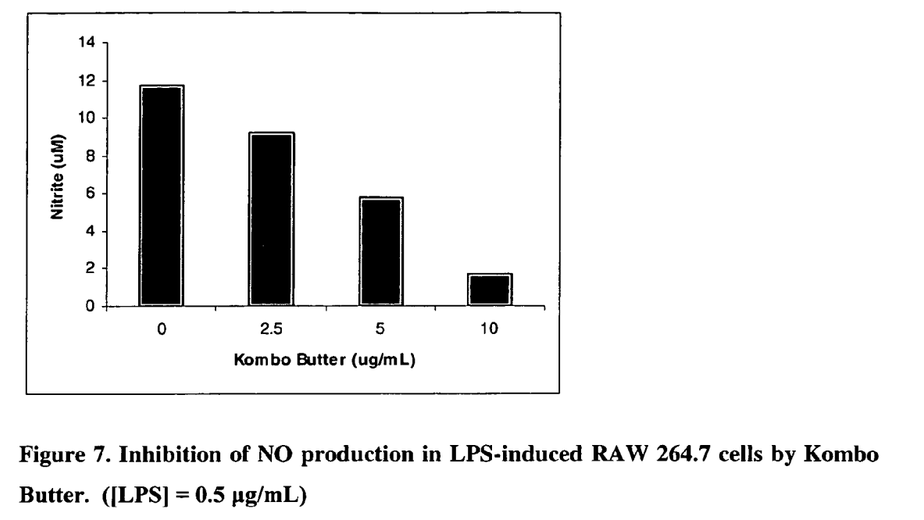
FIG. 7 shows the inhibitory effect of *Kombo* Butter on nitric oxide production in lipopolysaccharide-induced RAW 264.7 murine macrophage cells.
Figure 8:
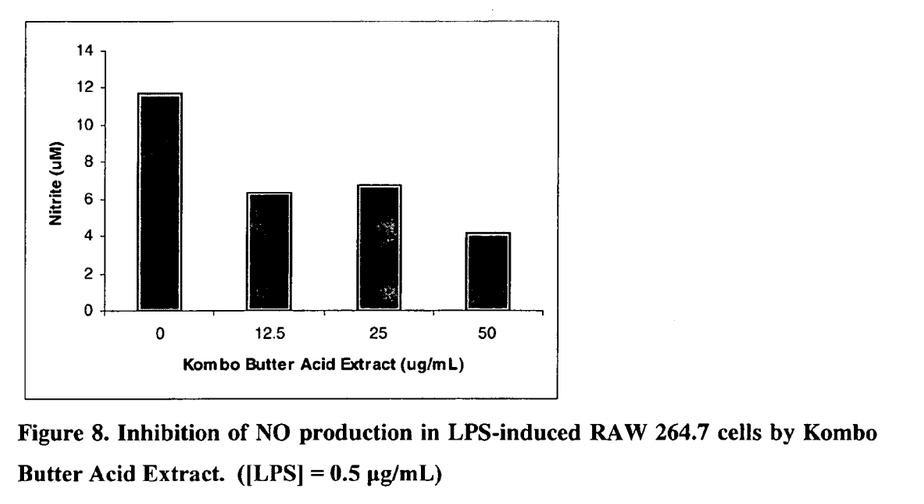
FIG. 8 shows the inhibitory effect of *Kombo* Butter Acid Extract on nitric oxide production in lipopolysaccharide-induced RAW 264.7 murine macrophage cells.

Subfraction 3 was further subjected to Sephadex LH-20 gel filtration chromatography using methanol as eluant. Subsequently, the major component was purified by preparative HPLC on a Phenomenex Phenyl-hexyl 30×250 mm, 10 um column with 60% acetonitrile:water as eluant at a flow rate of 10 ml/min to obtain 200 mg of pure sargahydroquinoic acid, also referred to herein as compound KB-3. Typical yields of purified sargahydroquinoic acid were 10-30% by weight of the *kombo* butter acid extract. The chemical structure of sargahydroquinoic acid is presented in FIG. 3.

Activities of *Kombo* Butter and its Constituents

We have determined that *kombo* butter, *kombo* butter acid extract, and purified sargaquinoic acid (KB-1), sargachromenol (KB-2), and sargahydroquinoic acid (KB-3) possess a variety of biological activities which correlate with a battery of health beneficial effects. Specifically, these activities include antioxidant activity as evidenced by radical scavenging in the 2,2'-diphenylpicrylydrazyl (DPPH) and 2,2'-azinobis-(3-ethylbenzothiazoline-6-sulfonic acid) (ABTS) assays, and anti-inflammatory activity as evidenced by their ability to inhibit (1) the production of nitric oxide (NO), (2) protein expression of inducible nitric oxide synthase (iNOS) and cyclooxygenase-2 (COX-2), and (3) mRNA expression of iNOS and COX-2 in lipopolysaccharide (LPS)-induced macrophage cells. These activities indicate the utility of these preparations and compounds in reducing the production of NO, iNOS protein and mRNA, and COX-2 protein and mRNA in induced cells either in vitro or in vivo, and also in giving rise to numerous beneficial health effects in human, animal, and avian subjects, including the treatment and prevention of cancers, particularly colon cancer, arthritis, including osteoarthritis, cardiovascular disease, high blood pressure, atherosclerosis, thromboembolic disease, fibromyalgia, irritable bowel syndrome or inflammatory bowel disease, cataracts, and conditions embodied by decreased cognitive functioning, including Alzheimer's disease as well as numerous other neurodegenerative conditions. Additionally, these agents are applicable to the treatment and prevention of numerous other adverse health conditions, including inflammatory and non-inflammatory rheumatoid and rheumatoid-like conditions as well as conditions embodied by chronic, acute, and/or transitory inflammation. The aforementioned activities are illustrated by way of the following non-limiting examples. Those skilled in the art will envision other modifications falling within the scope and spirit of the present invention as defined by the claims presented below.

EXAMPLE 1

Antioxidant Activity

*Kombo* butter, *kombo* butter acid extract, and purified sargaquinoic acid (KB-1), sargachromenol (KB-2), and sargahydroquinoic acid (KB-3) were tested for antioxidant activity by both the 2,2'-diphenylpicrylydrazyl (DPPH) and the 2,2'-azinobis-(3-ethylbenzothiazoline-6-sulfonic acid) (ABTS) free radical scavenging assays. A solution of DPPH in ethanol was prepared at a final concentration of $1.0 \times 10^{-4}$ M. Each of the potential actives under investigation was added to the DPPH solution at a number of different concentrations. The solutions were mixed, shaken vigorously and kept in the dark for half an hour. The absorbance of the samples was then measured at 517 nm with an HP Model 8453 spectrophotometer using a blank of ethanol without DPPH. All tests were run in triplicate and averaged. Differences among individual measurements were always less than 5% [26].

For the ABTS assay, a solution of ABTS in water was prepared at a final concentration of 7 mM. The ABTS radical cation (ABTS$^{\cdot+}$) was produced by adding solid potassium persulfate to the ABTS solution sufficient to yield a final concentration of 2.45 mM potassium persulfate in the mixture and allowing the mixture to stand in the dark at room temperature for 12-16 hours before use. The ABTS$^{\cdot+}$ solution was diluted with methanol to an absorbance of 0.70 at 734 nm. Stock solutions of each of the potential actives under investigation were diluted with ethanol to ensure 20-80% inhibition of the radical cation upon introduction of a 10 µL aliquot of the active solution to 1 ml of diluted ABTS$^{\cdot+}$ solution. The absorbance was measured beginning exactly 1 min after initial mixing and thereafter up to 6 min. Trolox was used as the standard, and the activity of each of the potential actives was expressed as a Trolox Equivalent Antioxidant Capacity (TEAC) value [26]. The TEAC value represents the millimolar concentration of a Trolox solution having an equivalent antioxidant capacity to a 1.0 mM solution of the potential active under investigation.

Purified sargachromenol and sargahydroquinoic acid were found to be very good DPPH free radical scavenging agents with IC$_{50}$ 17.3 and 9.0 ug/mL, respectively. Also, kombo butter acid extract, with an IC$_{50}$ of 25.2 ug/mL, was found to be a much better DPPH free radical scavenging agent than kombo butter. Similar results were found in the ABTS free radical scavenging assay, where sargahydroquinoic acid appeared as the most active compound. The results are listed in Table 1.

TABLE 1

Results of ABTS Free Radical Scavenging Assay

| Name | TEAC (mM) |
|---|---|
| Sargaquinoic acid (KB-1) | 0.15 |
| Sargachromenol (KB-2) | 0.75 |
| Sargahydroquinoic acid (KB-3) | 1.33 |
| Kombo butter acid extract | 400 mmol/Kg |
| Kombo butter | 1120 mmol/kg |

EXAMPLE 2

Inhibition of LPS-induced Nitric Oxide Production

The role of nitric oxide (NO) in the pathogenesis of various inflammatory diseases is well known. Endotoxins such as lipopolysachharide (LPS) have been shown to stimulate the production of NO from macrophages, which plays an important role in inflammation. Kombo butter, kombo butter acid extract, and purified sargaquinoic acid (KB-1), sargachromenol (KB-2), and sargahydroquinoic acid (KB-3) were tested for anti-inflammatory activity by assessment of their respective abilities to inhibit the production of NO from LPS-activated macrophages. Since the half-life of NO is very short, we measured nitrite as an indicator of the NO released from LPS-activated macrophages.

RAW 264.7 mouse macrophage cells were cultured in Dulbecco's Modified Eagle Medium (DMEM) supplemented with 15% fetal bovine serum (FBS) and an antibiotic and antimycotic mixture. Cell suspensions of 50,000 cells/well were cultured in quadruplicate in flat bottom microtiter plates for 12 hrs. Thereafter, 100 µl of media was replaced with fresh medium containing LPS (0.5 µg/mL) either alone or in combination with various concentrations of each of the potential actives under investigation and further cultured for 24 hrs. The culture supernatant was then collected and assayed for nitrite concentration as an indicator of NO production.

Culture supernatant (100 µl) was mixed with an equal volume of Griess reagent (SIGMA, MO, USA) and the absorbance was measured at 570 nm. The concentration of nitrite in each sample was calculated using a standard curve constructed from known concentrations of sodium nitrite dissolved in DMEM. The results presented in FIGS. 4 through 8 represent the mean values of 4 replicates from a single representative experiment. This experiment has been repeated 3 times with similar results. Thus, we have determined that kombo butter and its constituents significantly inhibit the LPS-induced production of nitric oxide by macrophages in a dose-dependent manner.

EXAMPLE 3

Inhibition of LPS-induced iNOS and COX-2 Protein Expression

To confirm whether the inhibition of NO production by kombo butter, kombo butter acid extract, and purified sargaquinoic acid (KB-1), sargachromenol (KB-2), and sargahydroquinoic acid (KB-3) was due to reduced enzymatic activity or protein expression of inducible nitric oxide synthase (iNOS), we investigated the effect of kombo butter and its constituents on iNOS protein expression by Western blotting. In addition to iNOS, we also studied the effect of kombo butter and its constituents on the expression of cyclooxygenase-2 (COX-2), an enzyme critical to the production of inflammatory prostaglandins and known to be activated in LPS-stimulated macrophages [14].

RAW 264.7 mouse macrophage cells were cultured in Dulbecco's Modified Eagle Medium (DMEM) supplemented with 15% fetal bovine serum (FBS) and an antibiotic and antimycotic mixture. Cell suspensions of 50,000 cells/well were cultured in quadruplicate in flat bottom microtiter plates for 12 hrs. Thereafter, 100 µl of media was replaced with fresh medium containing LPS (0.5 µg/mL) either alone or in combination with various concentrations of each of the potential actives under investigation and further cultured for 18 hrs.

An equal amount of protein (40 µg) from each sample was resolved by SDS-polyacrylamide gel electrophoresis. The resolved proteins were then transferred to a Hybond™ enhanced chemiluminescence nitrocellulose membrane (Amersham-Pharmacia Biotech, NJ, USA). The membrane was then incubated for 1 hr at room temperature with a blocking buffer containing 20 mM sodium phosphate buffer, pH 7.6, 150 mM NaCl, 0.1% Tween 20 and 5% nonfat dry milk. Thereafter, the membrane was incubated with primary antibody at 40° C. overnight, washed four times with PBST and further incubated with secondary antibody for 1 hr at room temperature. Specific bands were detected using enhanced chemiluminescence's detection system (Amersham-Pharmacia Biotech, NJ, USA) and the membrane was exposed to X-ray film. Densitometry was performed using image analysis software (SCION, NIH).

Figure 9:
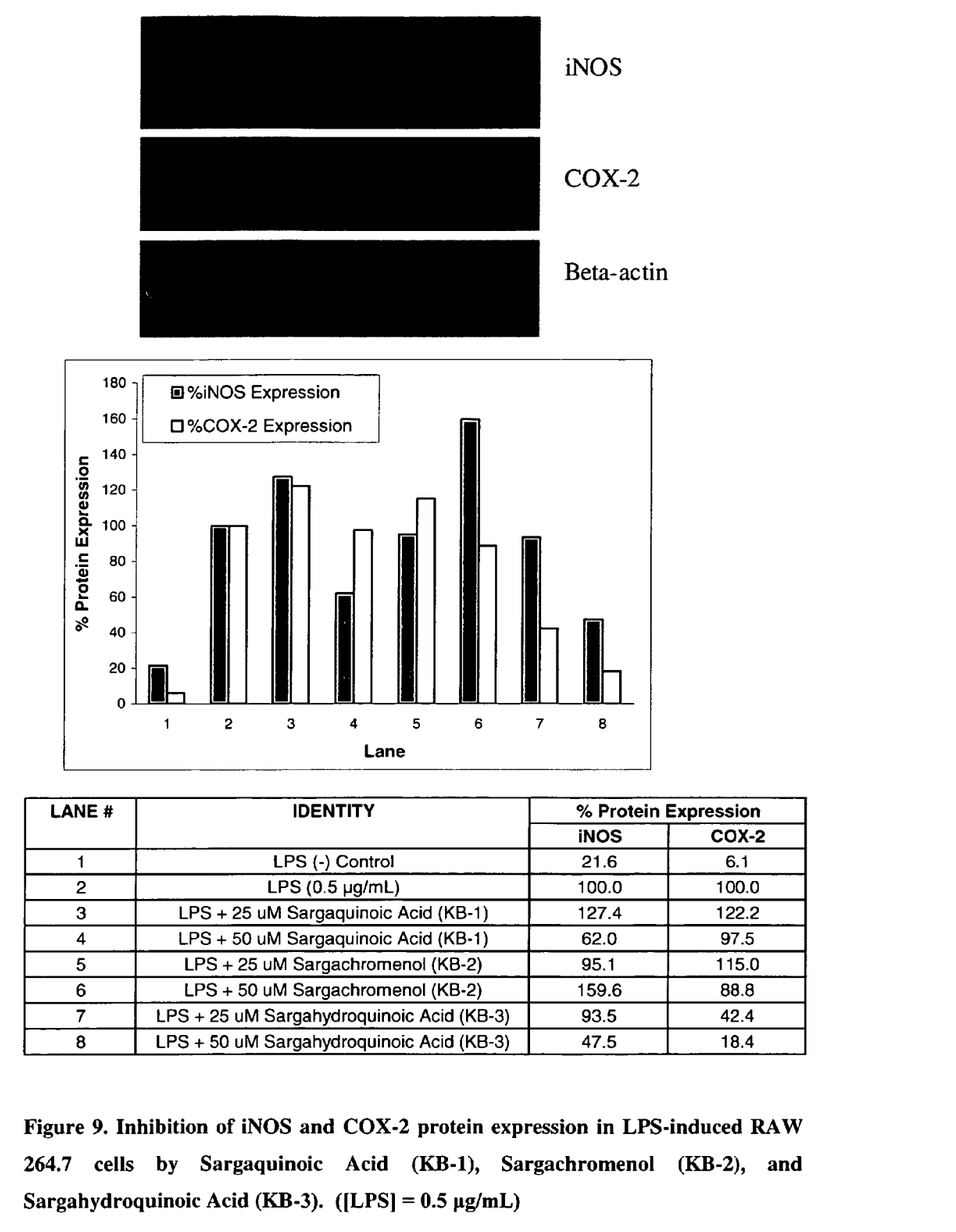
FIG. 9 shows the effects of Sargaquinoic acid (KB-1), Sargachromenol (KB-2), and Sargahydroquinoic acid (KB-3) on iNOS and COX-2 protein expression in lipopolysaccharide-induced RAW 264.7 murine macrophage cells.
Figure 10:
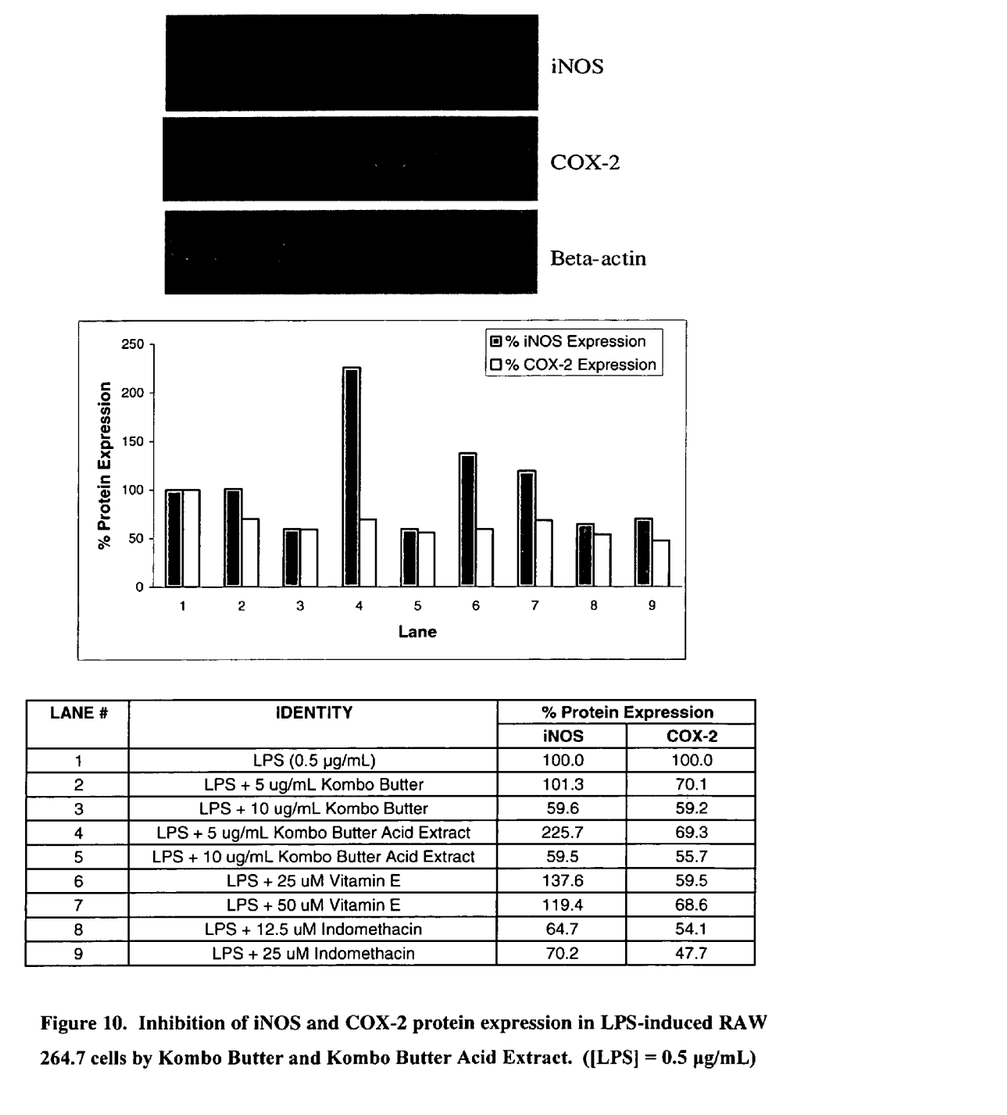
FIG. 10 shows the effects of *Kombo* Butter and *Kombo* Butter Acid Extract on iNOS and COX-2 protein expression in lipopolysaccharide-induced RAW 264.7 murine macrophage cells.

We found that kombo butter, kombo butter acid extract, sargaquinoic acid (KB-1) and sargahydroquinoic acid (KB-3) treatment for 18 hrs markedly inhibited iNOS protein expression in LPS-induced RAW 264.7 cells. The inhibitory concentrations of kombo butter and sargahydroquinoic acid for iNOS protein expression were similar to those for reduction of NO production. We also determined that kombo butter, kombo butter acid extract, sargachromenol (KB-2), and sargahydroquinoic acid (KB-3) treatment for 18 hrs markedly inhibited COX-2 protein expression in LPS-induced RAW 264.7 cells. The effects of sargaquinoic acid (KB-1), sargachromenol (KB-2), and sargahydroquinoic acid (KB-3) on iNOS and COX-2 protein expression are shown in FIG. 9, while those of *kombo* butter and *kombo* butter acid extract are shown in FIG. 10. The detection of β-actin was performed in the same blot as an internal control. These experiments have been repeated multiple times with similar observations.

EXAMPLE 4

Inhibition of LPS-induced iNOS and COX-2 mRNA Expression

To determine whether the inhibition of iNOS and COX-2 expression by *kombo* butter and its constituents is due to reduced protein synthesis or to modulation of post-translational events, we investigated the effects of *kombo* butter, *kombo* butter acid extract, and purified sargaquinoic acid (KB-1), sargachromenol (KB-2), and sargahydroquinoic acid (KB-3) on iNOS and COX-2 mRNA expression using RT-PCR analysis.

RAW 264.7 mouse macrophage cells were cultured ($10^6$/well) in a 6 well plate for 24 hrs followed by treatment with LPS (0.5 µg/mL) either alone or in combination with various concentrations of each of the potential actives under investigation for 12 hrs. Total RNA was isolated using Tri-reagent (Sigma, MO, USA) and 5 µg of this RNA was reverse transcribed to make cDNA using random hexamers and Superscript™ reverse transcriptase (Invitrogen, CA, USA) according to the manufacturer's instructions. The linear range of amplification of iNOS and COX-2 cDNA was determined using gene specific primers from Ambion, Inc. (TX, USA) according to the manufacturer's instructions. Briefly, the optimum amount of 18S primer and competitor for iNOS and COX-2 genes were determined. The PCR for iNOS (2 µl cDNA, 30 cycles) and COX-2 (1 µl cDNA, 25 cycles) was performed in a final volume of 50 µl containing dNTPs (each at 2.5 mM), 1×PCR buffer, 5 units of Taq DNA polymerase, 0.4 µM gene-specific primer, and an optimal ratio of 18S primer and competitor (3:7). Finally, PCR products from each sample (10 µl) were resolved by electrophoresis in a 2% agarose gel (Fisher Biotech, NJ, USA) and stained with ethidium bromide. An image of the gel was captured after the appropriate exposure time and densitometric analysis was performed using image analysis software (Scion, NIH). For relative quantification, 18S ribosomal RNA was also amplified in same reaction as an internal control. Quantitative analysis of the expression of iNOS and COX-2 mRNA was performed by taking the ratio of the integrated density of each band to that of the 18S RNA band in the same sample.

Figure 11:
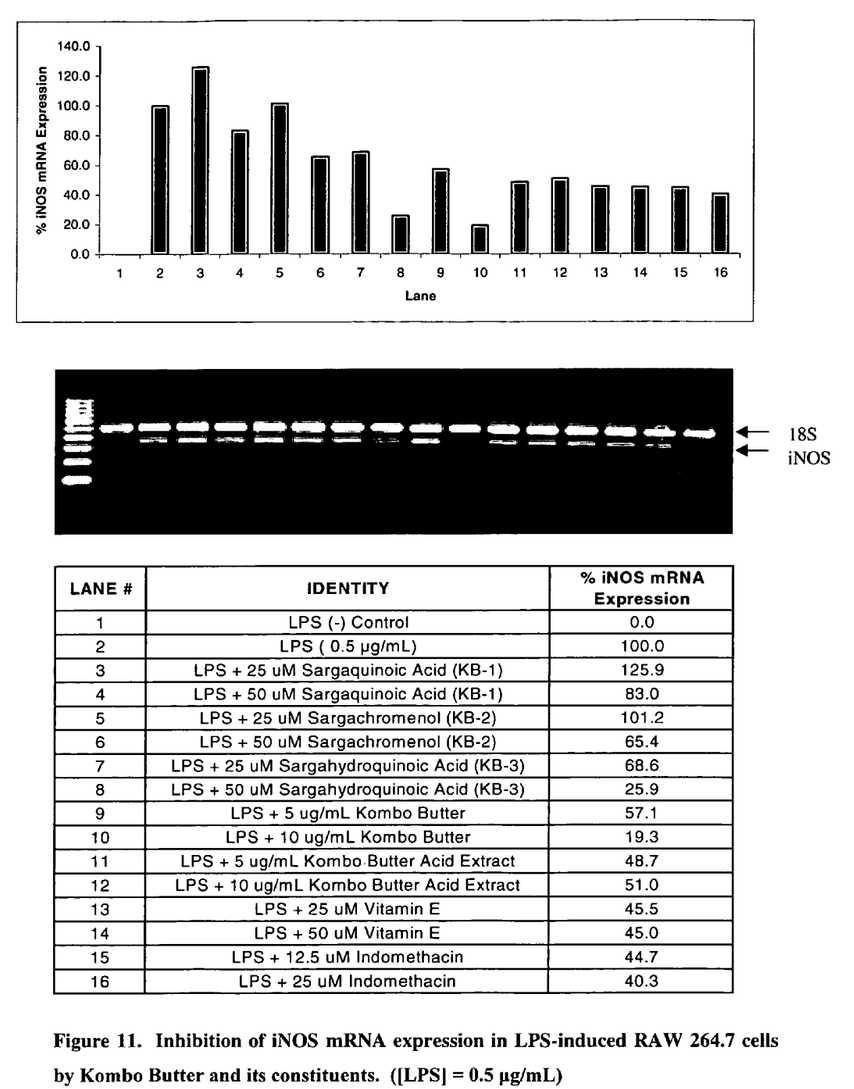
FIG. 11 shows the effects of *Kombo* Butter and its constituents on iNOS mRNA expression in lipopolysaccharide-induced RAW 264.7 murine macrophage cells.

We have observed that each of the active agents tested inhibited the expression of iNOS mRNA in LPS-induced RAW 264.7 mouse macrophage cells, as shown in FIG. 11. *Kombo* butter inhibited LPS-induced iNOS mRNA expression by approximately 43% at 5 µg/ml and 80% at 10 µg/ml, and sargahydroquinoic acid (KB-3) inhibited iNOS mRNA expression by 31% at 25 µM and 74% at 50 µM. These inhibitory activities correlate with the inhibition of iNOS protein expression by *kombo* butter and KB-3. Also noteworthy was the activity of *kombo* butter acid extract, which inhibited iNOS mRNA expression by approximately 50% at both 5 and 10 µg/ml. Moreover, sargaquinoic acid (KB-1) and sargachromenol (KB-2) both exhibited inhibitory activity at a concentration of 50 µM. Finally, vitamin E and the commercially available NSAID drug indomethacin were also included in the experiment as comparative controls. As is evident from the data in FIG. 11, the inhibitory activity of *kombo* butter and its constituents is in many instances comparable to and in some cases exceeds that of both vitamin E and indomethacin.

Figure 12:
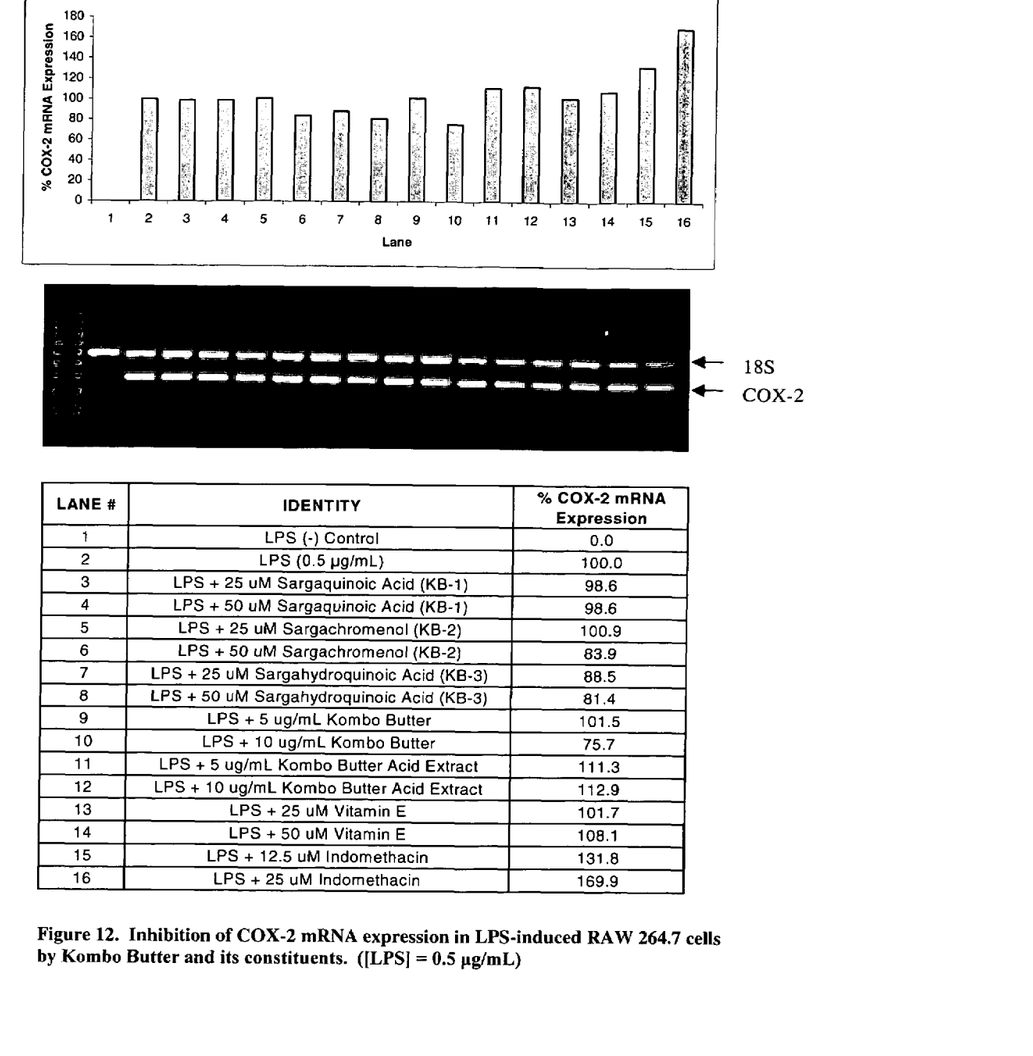
FIG. 12 shows the effects of *Kombo* Butter and its constituents on COX-2 mRNA expression in lipopolysaccharide-induced RAW 264.7 murine macrophage cells.

Our investigation of the effect of *kombo* butter and its constituents on COX-2 mRNA expression in LPS-induced RAW 264.7 mouse macrophage cells has revealed that *kombo* butter, sargachromenol (KB-2), and sargahydroquinoic acid (KB-3) possess inhibitory activity, as shown in FIG. 12. Specifically, *kombo* butter inhibited LPS-induced COX-2 mRNA expression by nearly 25% at 10 µg/ml, while sargachromenol (KB-2) inhibited COX-2 mRNA expression by 16% at a concentration of 50 µM. Interestingly, sargahydroquinoic acid (KB-3) inhibited COX-2 mRNA expression by nearly 12% at a concentration of 25 µM and by almost 19% at 50 µM. As with the experiment regarding iNOS mRNA expression, vitamin E and indomethacin were investigated as comparative controls, however, neither of these compounds effected any inhibition of COX-2 mRNA expression within the concentration ranges assayed.

REFERENCES

1 Xie, K. and Fidler, I. J. (1998) Therapy of cancer metastasis by activation of the inducible nitric oxide synthase. Cancer Metastasis Rev 17:55-75.

2 Nathan, C. and Xie, Q. W. (1994a) Nitric oxide synthases: roles, tolls, and controls. Cell 78: 915-918.

3 Nathan, C. and Xie, Q. W. (1994b) Regulation of biosynthesis of nitric oxide. J. Biol Chem 269:13725-13728.

4 Cook, H. T. and Cattell, V. (1996) Role of nitric oxide in immune-mediated diseases. Clin Sci 91:375-384.

5 Nguyen, T.; Brunson, D.; Crespi, C. L.; Penman, B. W.; Wishnok, J. S. and Tannenbaum, S. R. (1992) DNA damage and mutation in human cells exposed to nitric oxide in vitro. Proc Natl Acad Sci USA 89:3030-3034.

6 Wink, D. A.; Kasprzak, K. S.; Maragos, C. M.; Elespuru, R. K.; Misra, M.; Dunams, T. M.; Cebula, T. A.; Koch, W. H.; Andrews, A. W. and Allen, J. S. (1991) DNA deaminating ability and genotoxicity of nitric oxide and its progenitors. Science 254:1001-1003.

7 Miller, M. J.; Sadowska-Krowicka, H.; Chotinaruemol, S.; Kakkis, J. L.; and Clark, D. A. (1993) Amelioration of chronic ileitis by nitric oxide synthase inhibition. J. Pharmacol Exp Ther 264:11-16.

8 Kilbourn, R. G.; Gross, S. S.; Jubran, A.; Adams, J.; Griffith, O. W.; Levi, R. and Lodato, R. F. (1990) NG-methyl-L-arginine inhibits tumor necrosis factor-induced hypotension: implications for the involvement of nitric oxide. Proc Natl Acad Sci USA 87: 3629-3632.

9 Halliwell, B. (1994) Free radicals, antioxidants and human disease: curiosity, cause, or consequence. Lancet 344: 721-724.

10 Huang, H.-I. 1999, Inhibition of nitric oxide and cytokine production by curcumin, an antioxidative phytochemical, Rutgers, the State University of New Jersey Ph.D dissertation, pp 14-18.

11 Surh, Y. J.; Chun, K. S.; Cha, H. H.; Han, S. S.; Keum, Y. S.; Park, K. K. and Lee, S. S. (2001) Molecular mechanisms underlying chemopreventive activities of anti-inflammatory phytochemicals: down-regulation of COX-2 and iNOS through suppression of NF-kappa B activation. Mutat Res 480-481:243-268.

12 Lin, Y. L. and Lin, J. K. (1997) (−)-Epigallocatechin-3-gallate blocks the induction of nitric oxide synthase by down-regulating lipopolysaccharide-induced activity of transcription factor nuclear factor-kappaB. Mol Pharmacol 52:465-472.
13 Tsai, S. H.; Lin, S. Y. and Lin, J. K. (1999) Suppression of nitric oxide synthase and the down-regulation of the activation of NFkappaB in macrophages by resveratrol. Br. J. Pharmacol 126:673-680.
14 Liang, Y. C.; Huang, Y. T.; Tsai, S. H.; Lin, S. Y.; Chen, C. F. and Lin, J. K. (1999) Suppression of inducible cyclooxygenase and inducible nitric oxide synthase by apigenin and related flavonoids in mouse macrophages. Carcinogenesis 20:1945-1952.
15 Mshana, N. R. Floristic Studies in Ghana. (OUA/STRC publication, 2000) p 445.
16 Irvine, F. R. Woody Plants of Ghana with special reference to their uses. (Oxford University Press. 1961) pp 29-30.
17 Ayensu, E. S. Medicinal Plants of West Africa. (Reference Publications, Inc. 1978), pp 196-198.
18 Fort. D. M.; Ubillas, R. P.; Mendez, C. D.; Jolad, S. D.; Inman, W. D.; Carney, J. R.; Chen, J. L. Ianiro, T. T.; Hasbun, C.; Bruening, R. C.; Luo, J.; Reed, M. J.; Iwu, M.; Carlson, T. J.; King, S. R.; Bierer, D. E. Cooper, R. (2000) Novel antihyperglycemic terpene-quinones from *Pycnanthus angolensis*. Journal of Organic Chemistry 65 (20), 6534-6539.
19 Luo, J.; Cheung, J.; Yevich, E. M.; Clark, J. P.; Tsai, J.; Lapresca, P.; Ubillas, R. P.; Fort, D. M.; Carlson, T. J.; Hector, R. F.; King, S. R.; Mendez, C. D.; Jolad, S. D.; Reaven, G. M. (1999) Novel terpenoid-type quinines isolated from *Pycnanthus angolensis* of potential utility in the treatment of type 2 diabetes. Journal of Pharmacology and Experimental Therapeutics 288 (2), 529-534.
20 Njoku, C. J.; Hopp, D. C.; Alali, F.; Asuzu, I. U. Mclaughlin, J. L. (1997) Dihydroguaiaretic acid, a bioactive component of the stem bark of *Pycnanthus angolensis*. Planta Medica 63 (6), 580-581.
21 Omobuwajo, O. R.; Adesanya, S. A.; Babalola, G. O. (1992) Isoflavonoids from *Pycnanthus angolensis* and *Baphia nitida*, Phytochemsitry 31 (3), 1013-1014.
22 Atherton D. and Meara. M. I. The component Fatty Acids and Glycerides of some Myristica Fats. J. Soc. Chem. Ind. (London 1939) pp 353-357.
23 Eckey, E. W. Vegetable Fats and Oils. (Reinhold Publication, N.Y. 1954), p 412.
24 Lok, C. M.; Groenewegen, A.; Stroink J. B. A.; and Ward, J. P. (1983) Kombic acid, a hydroquinone polyisoprenoic carboxylic acid from *Pycnanthus kombo* seed fat. Phytochemistry 22, 1973-6.
25 Perez-Castorena, A. L.; Arciniegas, A.; Apan, M. T. R; Villasenor, J. L.; de Vivar, A. R. (2002) Evaluation of the anti-inflammatory and antioxidant activities of the plastoquinone derivatives isolated from *Roldana barba-johannis*. Planta Medica 68(7): 645-7.
26 Wang, M.; Shao, Y.; Li, J.; Zhu, N.; Rangearjan, M.; Lavoie, E. J.; and Ho, C. T. (1999) Antioxidant phenolic glycoside from Sage (*Salvia officinalis*). Journal of Natural Products 62, 454-456.

We claim:
1. A method for the preparation of a *kombo* butter acid extract from *kombo* butter, the method comprising:
   (i) Extraction of the *kombo* butter with a 70-100% ethanol:water portion to obtain a 70-100% ethanol:water fraction and a first residue;
   (ii) Separation of the 70-100% ethanol:water fraction and the first residue;
   (iii) Extraction of the 70-100% ethanol:water fraction with a first non-polar organic solvent portion;
   (iv) Separation of the 70-100% ethanol:water fraction and the first non-polar organic solvent portion;
   (v) Evaporation of the 70-100% ethanol:water fraction to obtain a crude *kombo* butter extract;
   (vi) Washing of the crude *kombo* butter extract with an aqueous solution comprising approximately 5-30% of an inorganic base to obtain a solution of *kombo* butter acid salts and a second residue;
   (vii) Separation of the solution of *kombo* butter acid salts and the second residue;
   (viii) Acidification of the solution of *kombo* butter acid salts to obtain a formulation of *kombo* butter acids;
   (ix) Extraction of the formulation of *kombo* butter acids with a second non-polar organic solvent portion to obtain an aqueous fraction and an organic fraction;
   (x) Separation of the aqueous fraction and the organic fraction; and
   (xi) Evaporation of the organic fraction to obtain the *kombo* butter acid extract.
2. The method of claim 1, further comprising
   (xii) Assay of the *kombo* butter acid extract to determine the concentration of a compound selected from the group consisting of sargaquinoic acid and sargachromenol.
3. The method of claim 1, further comprising
   (xii') Chromatographic separation of the *kombo* butter acid extract to obtain a compound selected from the group consisting of sargaquinoic acid and sargachromenol.
4. A method for the preparation of a *kombo* butter acid extract from African nutmeg seeds, the method comprising:
   (i) Milling the African nutmeg seeds to obtain a ground seed paste;
   (ii) Extraction of the ground seed paste with a 70-100% ethanol:water portion to obtain a 70-100% ethanol:water fraction and a first residue;
   (iii) Separation of the 70-100% ethanol:water fraction and the first residue;
   (iv) Extraction of the 70-100% ethanol:water fraction with a first non-polar organic solvent portion;
   (v) Separation of the 70-100% ethanol:water fraction and the first non-polar organic solvent portion;
   (vi) Evaporation of the 70-100% ethanol:water fraction to obtain a crude *kombo* butter extract;
   (vii) Washing of the crude *kombo* butter extract with an aqueous solution comprising approximately 5-30% of an inorganic base to obtain a solution of *kombo* butter acid salts and a second residue;
   (viii) Separation of the solution of *kombo* butter acid salts and the second residue;
   (ix) Acidification of the solution of *kombo* butter acid salts to obtain a formulation of *kombo* butter acids;
   (x) Extraction of the formulation of *kombo* butter acids with a second non-polar organic solvent portion to obtain an aqueous fraction and an organic fraction;
   (xi) Separation of the aqueous fraction and the organic fraction; and
   (xii) Evaporation of the organic fraction to obtain the *kombo* butter acid extract.
5. The method of claim 4, further comprising
   (xiii) Assay of the *kombo* butter acid extract to determine the concentration of a compound selected from the group consisting of sargaquinoic acid and sargachromenol.

6. The method of claim 4, further comprising
(xiii') Chromatographic separation of the *kombo* butter acid extract to obtain a compound selected from the group consisting of sargaquinoic acid and sargachromenol.

7. A method for the preparation of a *kombo* butter acid extract from African nutmeg seeds, the method comprising:
(i) Milling the African nutmeg seeds to obtain a ground seed paste;
(ii) Extraction of the ground seed paste with an aqueous solution comprising approximately 5-30% of an inorganic base to obtain a solution of *kombo* butter acid salts and a residue;
(iii) Separation of the solution of *kombo* butter acid salts and the residue;
(iv) Acidification of the solution of *kombo* butter acid salts to obtain a formulation of *kombo* butter acids;
(v) Extraction of the formulation of *kombo* butter acids with a non-polar organic solvent to obtain an aqueous fraction and an organic fraction;
(vi) Separation of the aqueous fraction and the organic fraction; and
(vii) Evaporation of the organic fraction to obtain the *kombo* butter acid extract.

8. The method of claim 7, further comprising
(viii) Assay of the *kombo* butter acid extract to determine the concentration of a compound selected from the group consisting of sargaquinoic acid and sargachromenol.

9. The method of claim 7, further comprising
(viii') Chromatographic separation of the *kombo* butter acid extract to obtain a compound selected from the group consisting of sargaquinoic acid and sargachromenol.

10. A method for reducing the production of at least one of nitric oxide, inducible nitric oxide synthase, and inducible nitric oxide synthase mRNA in at least one cell comprising the administration of a therapeutically effective amount of a composition comprising a chemical fraction from African nutmeg seeds, wherein the chemical fraction from African nutmeg seeds is a *kombo* butter acid extract, and wherein the *kombo* butter acid extract comprises from about 0.01 to about 1% by weight of sargaquinoic acid.

11. A method for reducing the production of at least one of nitric oxide, inducible nitric oxide synthase, and inducible nitric oxide synthase mRNA in at least one cell comprising the administration of a therapeutically effective amount of a composition comprising a chemical fraction from African nutmeg seeds, wherein the chemical fraction from African nutmeg seeds is a *kombo* butter acid extract, and wherein the *kombo* butter acid extract comprises from about 2 to about 6% by weight of sargachromenol.

12. A method for reducing the production of at least one of nitric oxide, inducible nitric oxide synthase, and inducible nitric oxide synthase mRNA in at least one cell comprising the administration of a therapeutically effective amount of a composition comprising a chemical fraction from African nutmeg seeds, wherein the chemical fraction from African nutmeg seeds consists essentially of saraquinoic acid and sarachromenol.

* * * * *